United States Patent [19]

Pang et al.

[11] Patent Number: 4,593,198

[45] Date of Patent: Jun. 3, 1986

[54] PULSE PILE-UP DISCRIMINATION SYSTEM

[75] Inventors: Sing C. Pang; Sebastian Genna, both of Belmont, Mass.

[73] Assignee: Digital Scintigraphics, Inc., Belmont, Mass.

[21] Appl. No.: 442,628

[22] Filed: Nov. 18, 1982

[51] Int. Cl.$^4$ .............................................. G01T 1/20
[52] U.S. Cl. ................................ 250/366; 250/363 S; 250/369
[58] Field of Search .................. 250/363 S, 369, 366, 250/370, 336.1, 394; 364/414

[56] References Cited

U.S. PATENT DOCUMENTS

| Re. 30,904 | 4/1982 | Miller et al. | 250/363 S |
|---|---|---|---|
| 3,525,047 | 8/1970 | Schwartz | 250/369 |
| 3,919,556 | 11/1975 | Berninger | 250/366 |
| 3,984,689 | 10/1976 | Arseneau | 250/369 |
| 4,217,496 | 8/1980 | Daniels et al. | 250/369 |

Primary Examiner—Alfred E. Smith
Assistant Examiner—Carolyn E. Fields

Attorney, Agent, or Firm—Joseph S. Iandiorio; William E. Noonan

[57] ABSTRACT

A pulse pile-up discrimination system for a multicell detector accumulates a charge on each cell to detect its response to a radiant emission impinging on an unknown position of the detector; the position of impingement of the radiant emission is established in accordance with the charge on each cell; a pulse pile-up discriminator provides, associated with each impingement position, lower and upper discrimination levels of a function of the distribution of charge on the cells indicative of a pulse pile-up; a function of the distribution of the charge on the cells is generated in response to the radiant emission impinging on the unknown position of the detector; the function of the distribution of charges on the cells in response to the radiant emission impinging on the unknown position of the detectors is compared to the lower and upper discrimination levels of a function of the distribution of charges provided by the pulse pile-up discriminator to determine whether a pulse pile-up has occurred.

4 Claims, 7 Drawing Figures

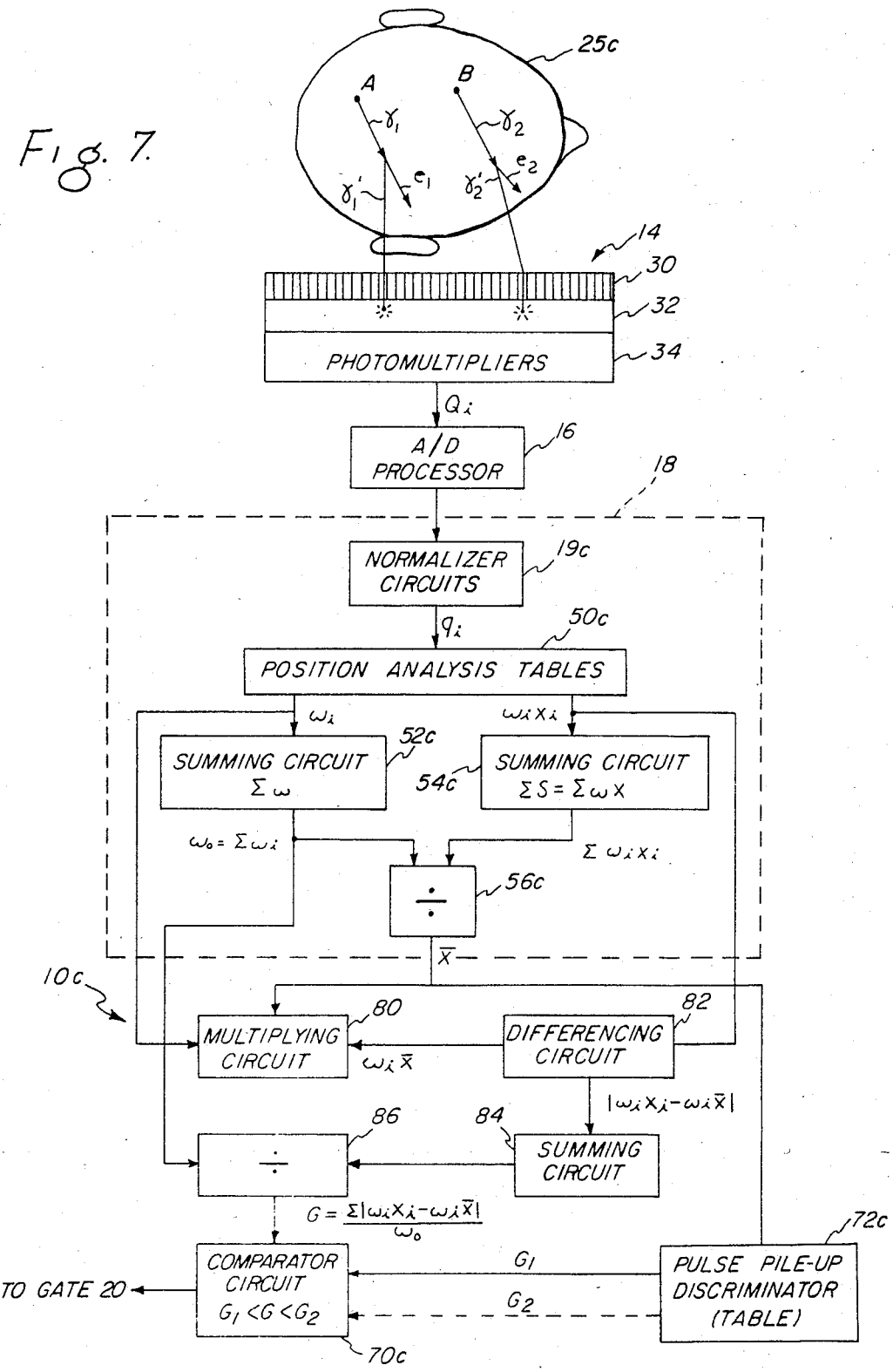

PULSE PILE-UP DISCRIMINATION SYSTEM

FIELD OF INVENTION

This invention relates to a pulse pile-up discrimination system for discrminating between single and multiple pulses derived from emissions in a multi-cell radiant emission detector.

BACKGROUND OF INVENTION

In conventional radionuclide emission scintillation cameras, gamma rays from a radioactive tracer in a body impinge upon and are absorbed by a sodium iodide scintillator. Such cameras, their calibration, and position analysis utilizing those cameras, is set forth in U.S. Pat. Nos. 4,095,107 and 4,228,515. An absorbed gamma ray causes excitation in the scintillator, with subsequent decay by means of light emissions with a half-life of two hundred fifty nanoseconds. These emissions are referred to as a scintillation event. Light from a scintillation event is distributed to an array of photomultiplier cells which are mounted on the surface of the crystal scintillator with a transparent light window. The position of a scintillation event is then determined by the charges in the pulses produced by the photomultiplier cells as a result of the absorption of scintillation light. At high count rates, some of the randomly occurring pulses overlap during the time needed to sample photomultiplier charges. This occurrence is referred to as pulse pile-up. When a pile-up of two or more events is accepted as a single event, a single erroneous position will be computed by the scintillation camera somewhere between the actual positions of the two events.

Presently, pulse pile-up events may be detected and rejected by two means: temporal and energy. The temporal technique rejects a perceived event if two or more pulses are detected within a sufficiently small interval of time such that they can both contribute to the pulse charge measurement significantly. The energy technique simply rejects events in which the total of the photomultiplier cell outputs exceeds some limit. Thus if the sum of the charges in the pulses from the photomultiplier cells is more than a prescribed amount, it is assumed that the charge was acquired from more than one event, and the input is rejected and no position determination is made based upon it. Although these techniques work alone and in combination in most applications, they may not be effective at high count rates in the range of tens to hundreds of thousands of counts per second. Under those conditions, an appreciable amount of multiple events or pulse pile-ups, may pass through both the temporal and the energy detection devices.

The problem is most acute when gamma rays are subjected to scattering in larger bodies. The scattering gives rise to Compton scattered photons, which are lower in energy than the original gamma ray emission. When two or more events occur close in time, their lower-energy Compton scattered photons may easily pass through the temporal window and the energy window as well.

SUMMARY OF INVENTION

It is therefore an object of this invention to provide an improved, reliable pulse pile-up discrimination system for discerning between single and multiple emission detections by a multicell detector of a radionuclide emission scintillation camera.

It is a further object of this invention to provide such a pulse pile-up discrimination system which can discriminate between single and multiple pulses even at higher pulse rates.

It is a further object of this invention to provide such a pulse pile-up discrimination system which can discriminate against pulse pile-ups caused by Compton scattering photons.

It is a further object of this invention to provide such a pulse pile-up discrimination system which relies on neither energy nor temporal discrimination.

It is a further object of this invention to provide such a pulse pile-up discrimination system which is a function of the photomultiplier pulse charge distribution.

The invention features a pulse pile-up discrimination system for a multicell detector. There are means for accumulating a charge on each cell to detect its response to a radiant emission impinging on an unknown position of the detector. Means responsive to the charges on each cell establish the perceived position of impingement of the radiant emission on the detector. A pulse pile-up discriminator, responsive to the means for establishing impingement, provides associated with each perceived impingement position lower and upper discrimination levels of a function of the distribution of charges on the cells indicative of a pulse pile-up. There are means for generating a function of the distribution of charge on the cells in response to the radiant emission impinging on the unknown position of the detector, and there are means for comparing the function of the distribution of charges on the cells in response to the radiant emission impinging on the unknown position of the detectors to lower and upper discrimination levels of a function of the distribution of charges provided by the pulse pile-up discriminator to determine whether a pulse pile-up has occurred.

In one embodiment the pulse pile-up discriminator provides lower and upper discrimination levels of charge spread ($D_1$ and $D_2$) indicative of pulse pile-up. The means for generating a function of the distribution of charge includes means for providing the cell charge moment distribution ($q_i C_i$); means responsive to the cell charge moment distribution for determining the centroid of cell charge distribution ($\lambda_0 = \Sigma q_i C_i$); means for determining the absolute difference between the cell position ($C_i$) and the centroid of cell charge ($\lambda_0$); means for multiplying the absolute value $|C_i - \lambda_0|$ by the cell charge $q_i$ to obtain the cell charge deviations $q_i |C_i - \lambda_0|$; and means for summing the cell charge deviations $q_i |C_i - \lambda_0|$ to obtain the cell charge spread (D). The means for comparing compares said charge spread (D) with the lower and upper discrimination levels of charge spread ($D_1$ and $D_2$) to determine whether a pulse pile-up has occurred.

In another embodiment, the means for establishing the position of impingement includes means for providing a weighting factor sum ($\omega_0$) representative of the response of the cells. The pulse pile-up discriminator provides lower and upper discrimination levels of a weighting factor sum ($V_1$ and $V_2$) which is a function of the charge ($q_i$) on a cell and the position ($C_i$) of the cell. The means for comparing compares the weighting factor ($\omega_0$) with lower and upper discrimination levels of weighting factor ($V_1$ and $V_2$) to determine whether a pulse pile-up has occurred.

In yet another embodiment the pulse pile-up discriminator provides at least lower and upper discrimination levels of position spread ($G_1$ and $G_2$). The means for establishing the position of impingement includes means for providing a weighting factor ($\omega_i$) representative of the response of each cell; a summation of the weighting factors ($\omega_0$); a weighted cell position ($\omega_i x_i$); and perceived impingement position $\bar{x}$. The means for generating a function of the distribution of charge includes means for providing the product of the impingement position ($\bar{x}$) and the weighting factor ($\omega_i$); means for determining the absolute difference $|\omega_i x_i - \omega_i \bar{x}|$ between the weighted position ($S = \omega_i x_i$) and the product of the weighting factor $\omega_i$ and impingement position ($\bar{x}$); means for summing said differences; and means for dividing the sum of the differences by the summation of said weighting factor ($\omega_0$) to obtain the weighted position spread $$(G = \frac{\Sigma|\omega_i x_i - \omega_i \bar{x}_i|}{\Sigma \omega_i}$$

The means for comparing compares the position spread (G) with the lower and upper discrimination levels of position spread ($G_1$ and $G_2$) to determine whether a pulse pile-up has occurred.

DISCLOSURE OF PREFERRED EMBODIMENT

Other objects, features and advantages will occur from the following description of a preferred embodiment and the accompanying drawings, in which:

FIG. 7 is a more detailed block diagram of a position spread embodiment of the pulse pile-up discrimination system according to this invention.

Figure 1:
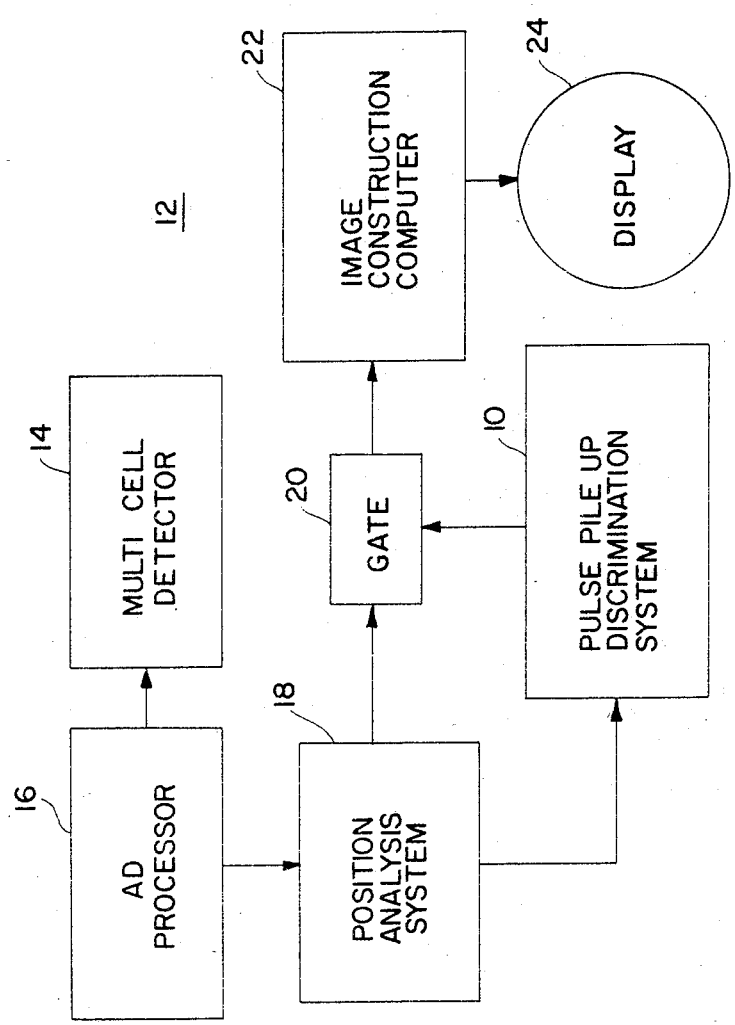
FIG. 1 is a block diagram of a radionuclide emission scintillation camera including the pulse pile-up discrimination system according to this invention.

There is shown in FIG. 1 a pulse pile-up discrimination system according to this invention in a radionuclide emission scintillation camera 12 which includes multicell detector 14, A/D processor 16, and position analysis system 18. Gate 20 is selectively enabled by pulse pile-up discrimination system 10 to pass or block the transfer of the emission position determined by system 18 to image construction computer 22 and display 24. A radiant emission is detected by multicell detector 14, whose output is converted from analog to digital by A/D processor 16. Position analysis system 18 then determines from that information the position of the emission. If pulse pile-up discrimination system 10 determines that the event was caused by the detection of more than one emission, it disables gate 20 and the position determined by system 18 is rejected. Conversely, if pulse pile-up discrimination system 10 determines that a pulse pile-up event has not occurred, then gate 20 is enabled to pass the position determined by system 18 to image construction computer 22. Multicell detector 14, A/D processor 16, and position analysis system 18 are all shown in greater detail in U.S. Pat. No. 4,228,515. That patent discloses a complete apparatus and technique for calibrating a radionuclide emission scintillation camera and for position analysis performed by such a camera, and the entire disclosure of U.S. Pat. Nos. 4,228,515 and 4,095,107 are incorporated herein by reference. Throughout the figures, like parts have been given like numbers and similar parts have been given like numbers accompanied by a lower case letter.

Figure 2:
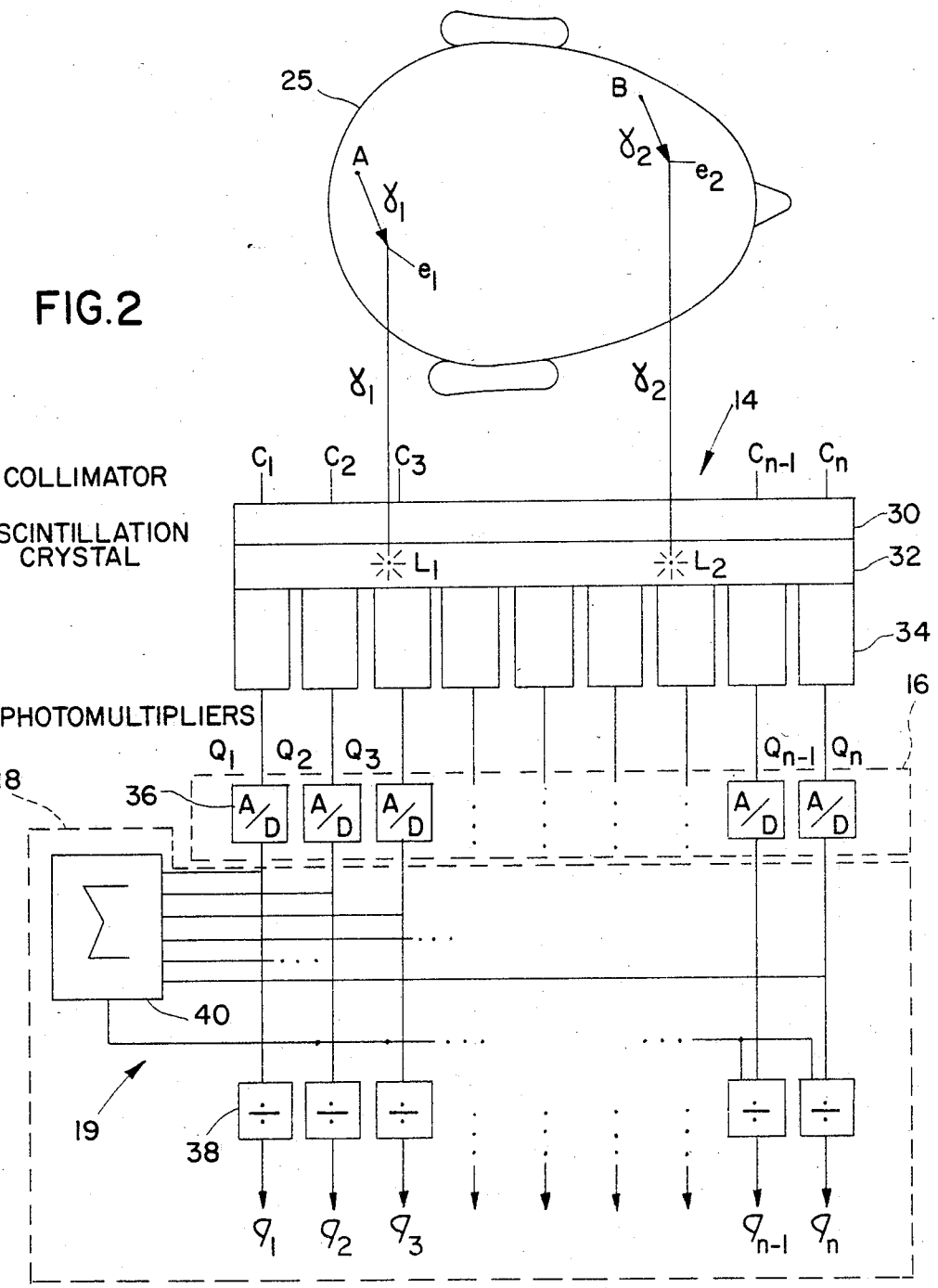
FIG. 2 is a more detailed diagram of portions of the multicell detector, A/D processor, and position analysis system of FIG. 1.

The occasion of a pulse pile-up condition is illustrated graphically in FIG. 2, where multicell detector 14 is shown to include collimator 30, scintillation crystal 32, and a number of photomultiplier cells 34. The position of each photomultiplier cell is defined as its center line position $C_1, C_2, \ldots C_n$. The analog output of each photomultiplier cell 34 is similarly designated $Q_1, Q_2, \ldots Q_n$. Position analysis system 18 includes among other things, normalizer circuits 19 including dividers 38 and summing circuit 40. The analog output of each photomultiplier cell 34 is delivered to one of a number of A/D converters 36 whose digital output is directed to an associated one of dividers 38 as well as to summing circuit 40. The sum of all of the digital outputs at A/D converters 36 is divided into the individual digital outputs of each of the A/D converters 36 in divider 38 to provide the digitized, normalized values $q_1, q_2, \ldots q_n$, representative of the output of each of photomultiplier cells 34 in response to a radionuclide emission impinging on the detector.

Two different emissions $\gamma_1$ and $\gamma_2$ occur nearly simultaneously at two different origins A and B in human head 25. If, as is typically the case in a large body such as a human body, Compton scattering occurs, gamma ray emission $\gamma_1$ yields a scattered electron, labelled $e_1$, and a scattered lower energy gamma ray, labelled $\gamma'_1$. A similar occurrence converts $\gamma_2$ into $e_2$ and $\gamma'_2$. Each of the scattered gamma rays $\gamma'_1$ and $\gamma'_2$ pass through collimator 30 and strike scintillator crystal 32 in areas $L_1$ and $L_2$, respectively, causing two scintillations to occur at approximately the same time and at reduced energy levels, so that discriminator devices which rely on temporal or energy readings will be deceived.

Figure 3:
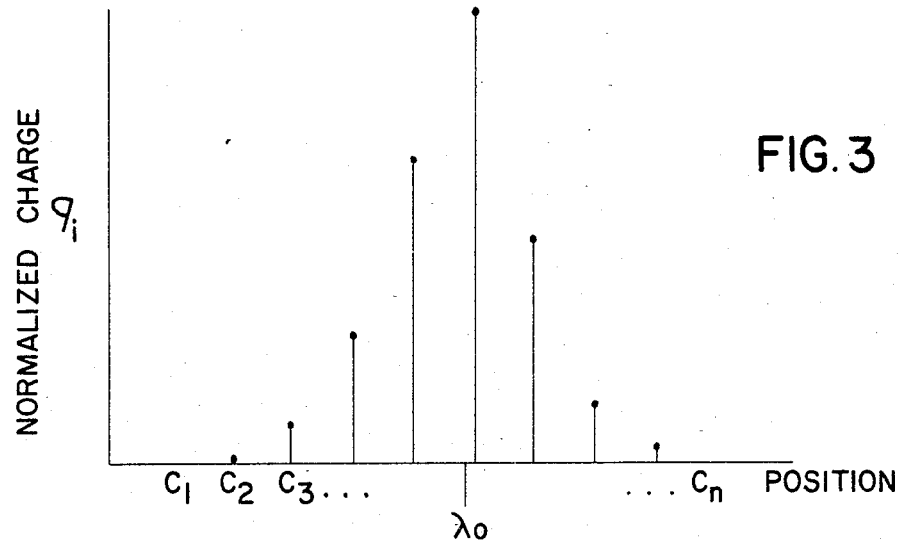
FIG. 3 is a graph of normalized charge versus cell position for a single emission event.

A single radionuclide emission event produces a distribution of charge, FIG. 3, so that the normalized charge dispersion across the position $C_1, \ldots C_n$ appears as shown in FIG. 3. In general, a bell-shaped distribution has the centroid of charge $\lambda_0$ in the vicinity of the maximum normalized charge $q_i$, which approximately represents the position of impingement of the emission.

Figure 4:
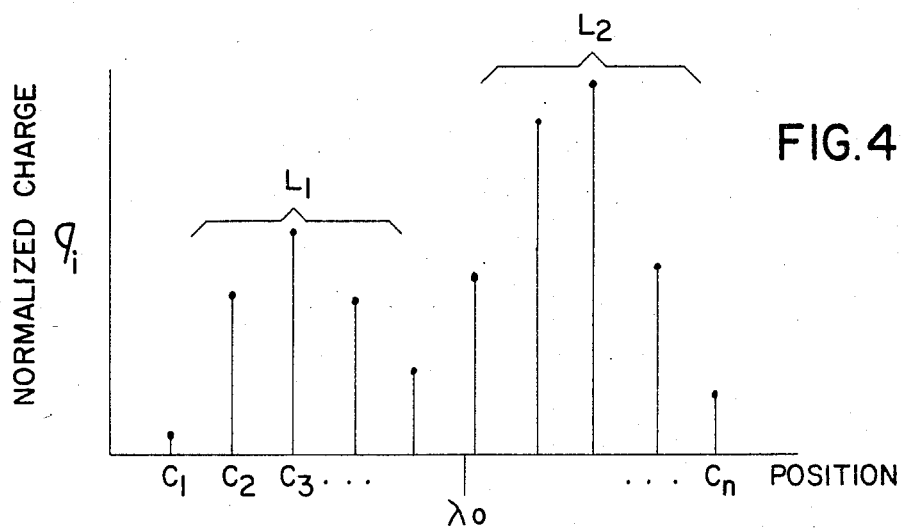
FIG. 4 is a graph similar to FIG. 3 for a pulse pile-up condition.

In contrast, in a pulse pile-up condition, as shown in FIG. 4, the distribution may take the form in which there is a first peaking in the area designated $L_1$ and a second peaking in the area designated $L_2$. This effects a centroid, $\lambda_0$, which occurs somewhere between positions $L_1$ and $L_2$ and results in an erroneous identification of the position of impingement of the emission.

To overcome this error, this invention provides for comparing a function of the distribution of charges on the cells to lower and upper discrimination levels of such a function in order to determine when a pulse pile-up condition has occurred.

The invention is herein disclosed in three different embodiments. In one, the function of the distribution of charges relates to the charge spread on the photomultiplier cells, FIG. 5. In the second, it relates to the weighting factor sum spread, FIG. 6, and in the third, the position spread, FIG. 7.

Figure 5:
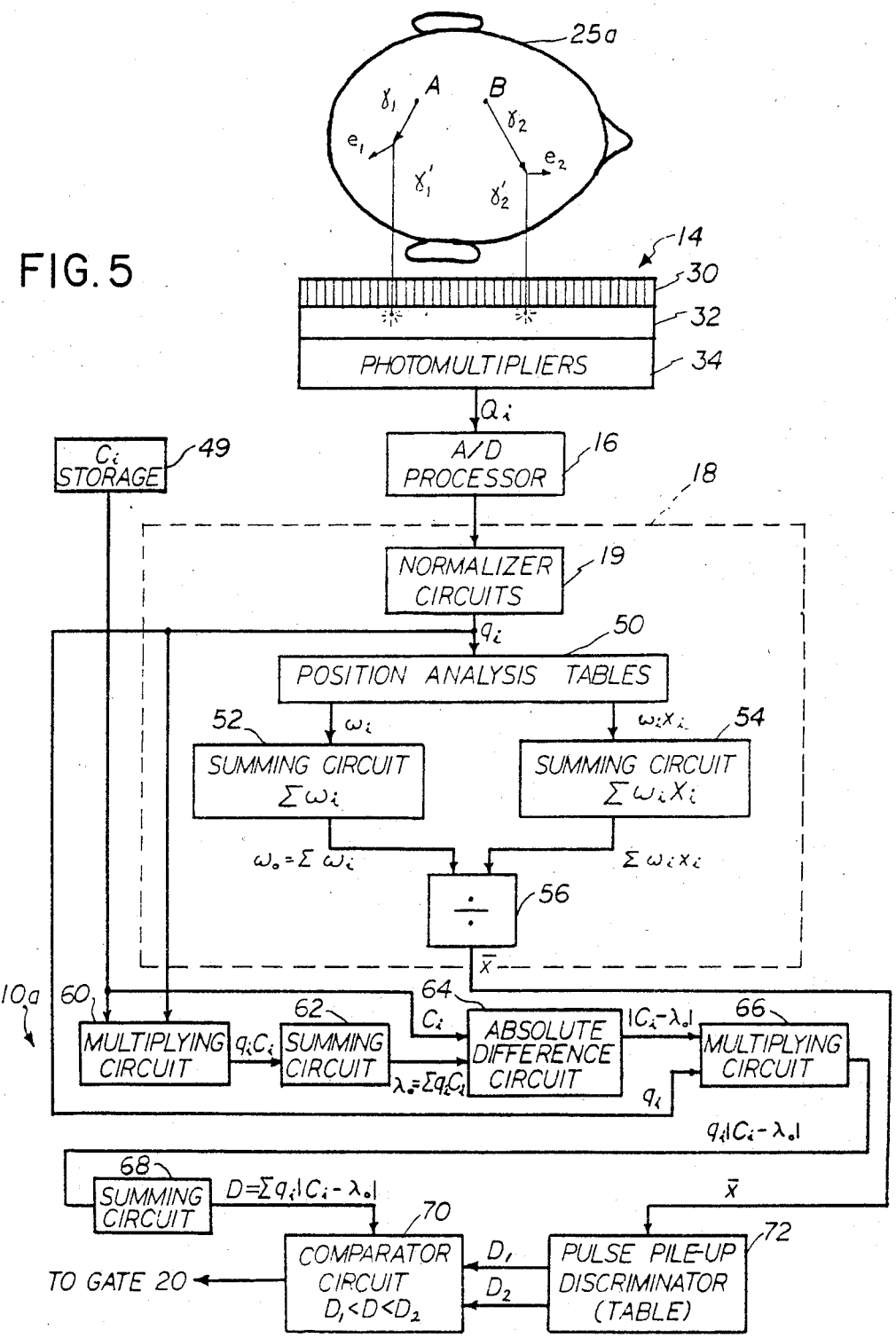
FIG. 5 is a more detailed block diagram of a cell charge spread embodiment of the pulse pile-up discrimination system according to this invention.

In the charge spread approach, FIG. 5, the $Q_i$ output from photomultipliers 34 is fed directly to A/D processor 16, whose digital output is directed to normalizer circuits 19, which provides a normalized digitized output $q_i$.

The normalized, digitized charge values $q_i$ are delivered to position analysis tables 50 which, in response to the value of the charge inputs, provide various values of the weighting factor $\omega_i$ to summing circuit 52, and various values of weighted positions $S_i$, also referred to as $\omega_i x_i$, to summing circuit 54. The summation of $\omega_i x_i$ is divided by the summation of $\omega_i$, or $\omega_0$ in circuit 56 to provide the perceived impingement position $\bar{x}$. A/D processor 16 is shown in greater detail in "FIG. 10" of U.S. Pat. No. 4,228,515. The photomultiplier cell position information $C_i$ is provided by storage circuit 49. Normalizer circuits 19, position analysis tables 50, summing circuits 52 and 54, and divider circuit 56, are all part of the position analysis system 18, which corresponds to the "position analysis system 140" of U.S. Pat. No. 4,228,515. For example, normalizer 19 corresponds to "normalizer circuits 42"; position analysis table 50 corresponds to the "storage circuits 54 including tables 150" of the patent; summing circuits 52 and 54 refer to "summing circuits 152 and 154" of the patent; and divider 56 refers to "divider circuit 156" of the patent. Portions of the position analysis system have been omitted for simplicity since they are contained in the disclosure of U.S. Pat. No. 4,228,515, which has been fully incorporated herein by reference. The nomenclature in FIG. 5 has been changed somewhat by the addition of the subscript i, which is not used in the patent, and the addition of $\omega_0$ to represent the summation of $\omega_i$.

Pulse pile-up discriminator circuit 10a includes multiplier circuit 60, which multiplies together the normalized charge $q_i$ and position $C_i$ to obtain the cell charge moment $q_i C_i$. The cell charge moment, $q_i C_i$, is delivered to summing circuit 62 which provides the centroid, $\lambda_0$, of the cell charge distribution, that is, the summation of $q_i C_i$. The absolute difference between the photomultiplier cell positions, $C_i$, and the cell charge distribution centroid $\lambda_0$ is found in differencing circuit 64, $|C_i - \lambda_0|$, and multiplied by normalized cell charge, $q_i$, in circuit 66. Their summation is accumulated by summing circuit 68 to produce the spread of the cell charge, D, about the centroid: $D = \Sigma q_i |C_i - \lambda_0|$. This charge spread value D is then submitted to comparator circuit 70, which compares the value D with one or both of the charge spread limits $D_1$, $D_2$. If comparator circuit 70 determines that charge spread value D is larger than charge spread limit $D_2$ or smaller than the charge spread limit $D_1$, then a determination has been made that a pulse pile-up condition exists, and a signal is delivered to gate 20 to reject the position $\bar{x}$ submitted by position analysis system 18. If, in contrast, the charge spread value D is between $D_1$ and $D_2$, then the determination is that a single event has occurred, and the signal is provided to gate 20 to enable it to pass the $\bar{x}$ position from position analysis system 18 to image construction computer 22. Although two limits, $D_1$ and $D_2$, are shown provided by pulse pile-up discriminator 72, this is not a necessary limitation of the invention, for only one limit, $D_2$, may be necessary. That limit can be set so that if the charge spread D is larger than the limit a pulse pile-up condition is indicated and the $\bar{x}$ position is rejected, whereas if the charge spread value D is smaller than the limit $D_2$, a single event is indicated and the $\bar{x}$ position can be accepted.

The pulse pile-up discriminator may include a circuit for calculating the limit $D_1$ and/or $D_2$ according to a selected criteria. More typically, as indicated in FIG. 5, it is a table of values which have been obtained empirically from single scintillation events by operating the components in FIG. 5 to obtain data for the value D from summing circuit 68, with gamma rays impinging at each scintillating position, x, a number of times, and determining from that empirical data the desired cutoff to separate the probable pulse pile-up events from the probable single events.

Figure 6:
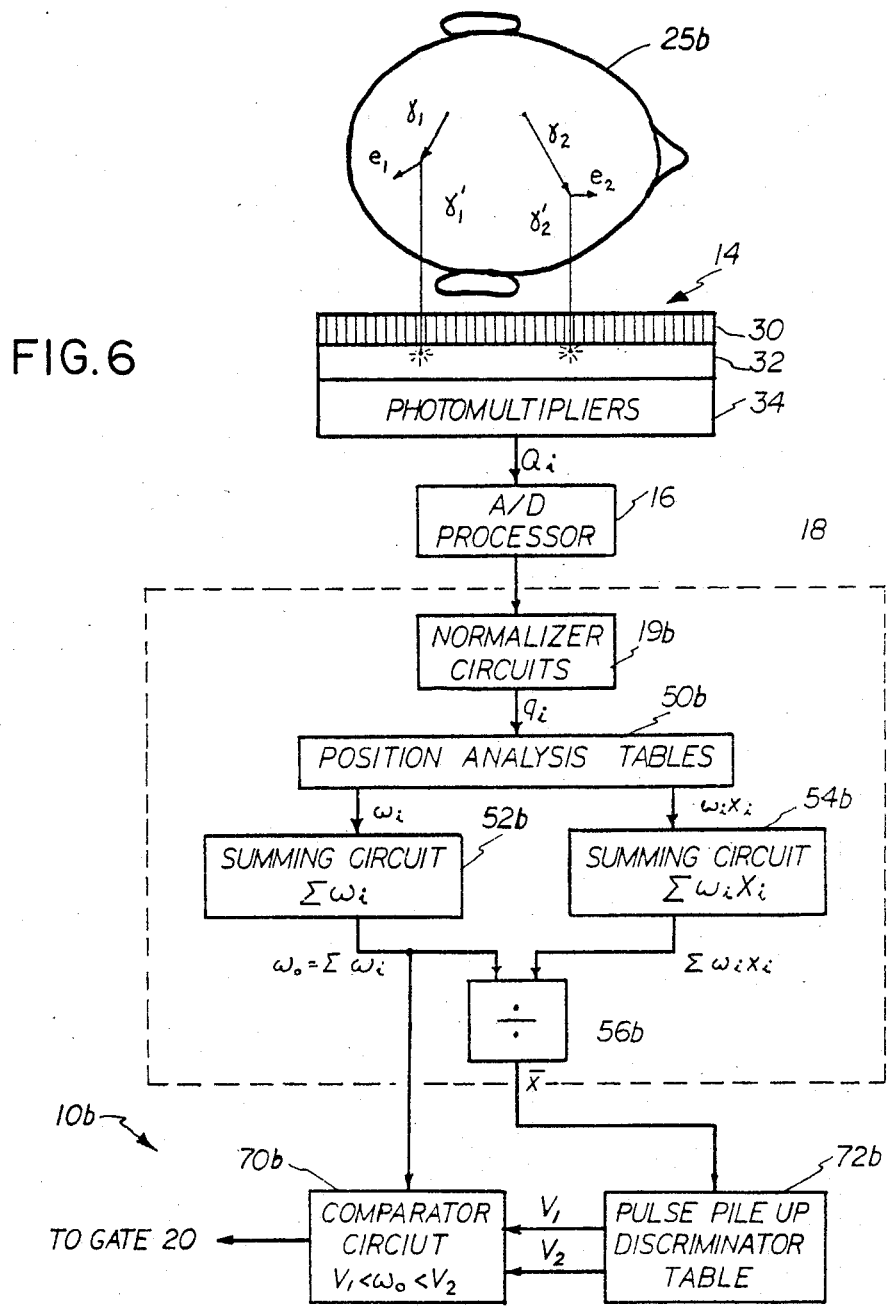
FIG. 6 is a more detailed block diagram of a weighting factor sum spread embodiment of the pulse pile-up discrimination system according to this invention.

The weighting sum spread approach is shown in FIG. 6, where pulse pile-up discrimination system 10b includes pulse pile-up discriminator 72b, which stores at least one weighting factor limit $V_1$ associated with each $\bar{x}$ position similar to the operation of discriminator 72 of FIG. 5. The weighting factor limits $V_1$ and $V_2$, or at least one of them, as explained previously with respect to FIG. 5, is submitted to comparator circuit 70b, which also receives the summation $\omega_0$ of all of the weighting factors $\omega_i$ from summing circuit 52b. If comparator circuit 70b determines that $\omega_0$ is smaller than the weighting factor limit $V_1$, or larger than the weighting factor limit $V_2$, then a pulse pile-up condition is indicated and a signal to gate 20 disables it from passing the $\bar{x}$ determination made by position analysis system 18.

The position spread approach, FIG. 7, utilizes the impingement position $\bar{x}$ and the weighting factor $\omega_i$, multiplied together in multiplier circuit 80 to produce a weighted perceived impingement position $\omega_i \bar{x}$. The absolute difference between the weighted impingement position $\omega_i \bar{x}$ and the weighted position determined from each cell normalized charge $\omega_i x_i$ is determined in differencing circuit 82 and submitted to summing circuit 84, which delivers the sum of those absolute differences to divider circuit 86. In divider circuit 86 the sum of those absolute differences is divided by the sum of the weighting factors $\omega_0$ to obtain the position spread G. The position spread G is compared to one or two limits of position spread $G_1$, $G_2$ in comparator circuit 70c. If the position spread G is lower than limit $G_1$ or higher than $G_2$, this indicates that a pulse pile-up condition has occurred and a signal is provided to gate 20 to prevent the passage of the position determination signal from position analysis system 18. Otherwise, gate 20 is enabled to pass the impingement position determination from position analysis system 18. As with discrimination systems 10b and 10a, only one limit may be necessary and the limits may be provided by storage in a table by values determined empirically by operations of the device to obtain G data from circuit 86 from single scintillation events at each of the positions, x, a number of times, and determining from that empirical data the desired cutoff to separate the probable pulse pile-up events from the probable single events.

Although the invention has been disclosed herein showing only a one-dimensional extension of the photomultiplier cells, this is not a necessary limitation of the invention, for two-dimensional, square, cylindrical or other shapes and other arrangements of photomultiplier cells may be used, as disclosed in the referenced Pat. Nos. 4,228,515 and 4,095,107.

The specific circuits defined in the embodiments of FIGS. 5, 6 and 7 are only illustrative and not limiting. For example, in FIG. 5 the absolute difference, circuit 64, which produces the output $|C_i - \lambda_0|$ could be replaced by one which produces the output $(C_i-\lambda_0)^2$. Other variations are possible with the system of FIG. 5, and FIGS. 6 and 7 as well.

Other embodiments will occur to those skilled in the art and are within the following claims.

What is claimed is:

1. A pulse pile-up discrimination system for a multi-cell detector comprising:

means for accumulating a charge on each cell to detect its response to a radiant emission impinging on an unknown position on the detector;

means, responsive to the charge on each cell, for establishing the position of impingement of the radiant emission on the detector;

a pulse pile-up discriminator, responsive to said means for establishing the position of impingement, for providing associated with each impingement position at least lower and upper discrimination levels of a function of the distribution of charge on the cells indicative of a pulse pile-up;

means for generating a function of the distribution of charge on the cells in response to said radiant emission impinging on said unknown position of said detector; and means for comparing said function of the distribution of charges on the cells in response to said radiant emission impinging on said unknown position of said detectors to said lower and upper discrimination levels of a function of the distribution of charges provided by said pulse pile-up discriminator to determine whether a pulse pile-up has occurred.

2. The system of claim 1 in which said pulse pile-up discriminator provides upper and lower discrimination levels of charge spread indicative of pulse pile-up; said means for generating a function of the distribution of charge includes means for providing the cell charge moment distribution; means responsive to the cell charge moment distribution for determining the centroid of cell charge distribution; means for determining the absolute difference between the cell position and the centroid of cell charge; means for multiplying the absolute value by the cell charge to obtain the cell charge deviations; and means for summing the cell charge deviations to obtain the cell charge spread; and said means for comparing compares said charge spread with said lower and upper discrimination levels of charge spread to determine whether a pulse pile-up has occurred.

3. The system of claim 1 in which said means for establishing the position of impingement includes means for providing a weighting factor sum representative of the response of the cells; said pulse pile-up discriminator provides lower and upper discrimination levels of a weighting factor sum which is a function of the charge on a cell and the position of the cell; and said means for comparing compares said weighting factor with said lower and upper discrimination levels of a weighting factor to determine whether a pulse pile-up has occurred.

4. The system of claim 1 in which said pulse pile-up discriminator provides at least lower and upper discrimination levels of position spread; said means for establishing the position of impingement includes means for providing a weighting factor representative of the response of each cell, a summation of the weighting factors, a weighted cell position and perceived impingement position; said means for generating a function of the distribution of charge includes means for providing the product of the impingement position and the weighting factor; means for determining the absolute difference between the weighted position and the product of the weighting factor and impingement position; means for summing said differences; and means for dividing the sum of the differences by the summation of said weighting factor to obtain the weighted position spread and said means for comparing compares said position spread with said lower and upper discrimination levels of a position spread to determine whether a pulse pile-up has occurred.

* * * * *